United States Patent [19]

Hayashi et al.

[11] 4,071,534

[45] Jan. 31, 1978

[54] PROCESS FOR PRODUCING L-ASCORBIC ACID-2-SULFATE

[75] Inventors: Eiichi Hayashi, Shizuoka; Kiyoshi Takita, Shimizu; Hironari Sugiyama, Shimizu; Yukio Nezu, Shimizu, all of Japan

[73] Assignee: Kumiai Chemical Industry Co., Ltd., Tokyo, Japan

[21] Appl. No.: 711,410

[22] Filed: Aug. 3, 1976

Related U.S. Application Data

[63] Continuation-in-part of Ser. No. 521,767, Nov. 7, 1974, abandoned.

[30] Foreign Application Priority Data

| | | |
|---|---|---|
| Nov. 7, 1973 | Japan | 48-124395 |
| Nov. 8, 1973 | Japan | 48-124951 |
| Oct. 29, 1974 | United Kingdom | 46760/74 |
| Aug. 21, 1975 | United Kingdom | 34845/75 |
| Nov. 6, 1974 | Germany | 2452719 |
| Nov. 6, 1974 | France | 74 36797 |
| Nov. 4, 1974 | Canada | 212951 |
| Nov. 6, 1974 | Switzerland | 14919/74 |
| Nov. 6, 1974 | U.S.S.R. | 2075017/234 |

[51] Int. Cl.$^2$ ............................................. C07D 307/62
[52] U.S. Cl. ............................................. 260/343.7
[58] Field of Search ............................................. 260/343.7

[56] References Cited

FOREIGN PATENT DOCUMENTS

7,430,354  3/1974  Japan .............................. 260/343.7

OTHER PUBLICATIONS

Gilbert, Sulfonation & Related Reactions (Interscience, 1965), p. 374.
Quadri, Diss. Abstr. Int. B, Mar. 1974, 34(9), 4431–4432.
Quadri, et al., Carbohyd. Res., 1973, 29(1), 259–264.

*Primary Examiner*—Cecilia M. S. Jaisle
*Attorney, Agent, or Firm*—Oblon, Fisher, Spivak, McClelland & Maier

[57] ABSTRACT

A process for producing a mono- or di-alkali metal salt or alkaline earth metal salt of L-ascorbic acid-2-sulfate which comprises reacting L-ascorbic acid in which the 5 and 6 positions are protected by a ketone or aldehyde, with dimethyl formamide-sulfur trioxide complex, which is produced by a reaction of dimethyl formamide with chlorosulfonic acid and a dehydrohalogenating agent such as pyridine, triethylamine, dimethyl aniline, which is a tertiary amine so as to produce a sulfate, and neutralizing the product with an alkali metal hydroxide or an alkaline earth metal hydroxide, and removing said protecting aldehyde or ketone at 5- and 6-positions.

6 Claims, No Drawings

PROCESS FOR PRODUCING L-ASCORBIC ACID-2-SULFATE

REFERENCE TO RELATED APPLICATION

This application is a continuation-in-part of Ser. No. 521,767, filed Nov. 7, 1974, and now abandoned.

BACKGROUND OF THE INVENTION

1. Field of the Invention

The present invention relates to a process for economically producing L-ascorbic acid-2-sulfate and salts thereof of high purity in high yield. These compounds are useful as medicines, domestic medicines, animal medicines and as additives for food, feed and cosmetic materials.

2. Description of the Prior Art

The synthesis of salts of L-ascorbic acid-sulfate has been demonstrated by reaction of pyridine-sulfur trioxide complex with 5,6-O-benzylidene-L-ascorbic acid and then converting the product to the potassium salt thereof. [T. M. Chu et al. Steroids 1968, 12, (3) 309–321; S. F. Quadri, Diss Abstr. Int, B, Vol. 34 (9) 4431 – 4432 (1974); S. F. Quadri, et.al., Carbonhyd. Res. Vol. 29 (1) 259 – 264 (1973); Murata Japanese Unexamined Patent Publication No. 30354/1974 (1974)]. However, the yield from such process has been low, and high purity products could not be obtained. Accordingly, a need exists to provide a method by which L-ascorbic acid-L-sulfate and salts thereof, can be produced economically in high yields and high purity.

SUMMARY OF THE INVENTION

Accordingly, it is an object of the present invention to provide a process for producing L-ascorbic acid-2-sulfate or a salt thereof having high purity in an industrial and economical manner. The object of the present invention has been attained by reacting L-ascorbic acid, having the 5- and 6-positions protected by a ketone or aldehyde, with dimethyl formamide-sulfur trioxide complex, neutralizing the product with an alkali metal hydroxide or an alkaline earth metal hydroxide and acidifying the product to remove the protecting substituent at the 5- and 6-positions.

DETAILED DESCRIPTION OF THE PREFERRED EMBODIMENTS

In this process, L-ascorbic acid is employed in which the 5-and 6-positions are protected by a ketone e.g. acetone, methylethyl ketone, diisopropyl ketone, cyclohexanone, and benzophenone or an aldehyde e.g. acetaldehyde, propionaldehyde, benzaldehyde, chlorobenzaldehyde or methyl benzaldehyde. The L-ascorbic acid having such protecting substituent is treated with dimethyl formamide-sulfur trioxide which is produced by a reaction of dimethyl formamide with chlorosulfonic acid and a dehydrohalogenating agent such as pyridine triethylamine, dimethyl aniline which is tertiary amine. The alkali metal salt of L-ascorbic acid having a protecting substituent at the 5- and 6-positions can be treated with the dimethyl formamidesulfur trioxide complex and an inert solvent including excess dimethyl formamide.

The sulfated product may be neutralized with an alkali metal hydroxide or an alkaline earth metal hydroxide to form a di-alkali salt of L-ascorbic acid sulfate having a protecting substituent at the 5- and 6-positions. The product can then be acidified with an inorganic acid e.g. sulfuric acid, hydrochloric acid or an organic acid e.g. acetic acid to remove the protecting substituent at the 5- and 6-positions and to produce mono-alkali metal salts of L-ascorbic acid-2-sulfate. If desired, 2,3-dialkali metal salts of L-ascorbic acid-2-sulfate can be produced by further reaction with an alkali metal hydroxide.

A tertiary amine such as pyridine, triethylamine, dimethyl aniline, etc. should be added after mixing dimethyl formamide with chlorosulfonic acid or it should be added to dimethyl formamide before contacting with chlorosulfonic acid so as to form dimethyl formamidesulfur trioxide complex.

In the reaction, 1 – 2 moles of the dimethyl formamide-sulfur trioxide complex to 1 mole of the L-ascorbic acid having a protecting substituent at 5- and 6-positions is used. The reaction temperature of the sulfation is in a range of −40° to 100° C, preferably 10 to 40° C, and the reaction time is from 1/6 – 20 hours. The solvating medium can be dimethyl formamide, dioxane, tetrahydrofuran, or the like. After the sulfation, the product is neutralized using an alkali metal hydroxide or an alkaline earth metal hydroxide at low temperature, to produce the mono-alkali metal or alkaline earth metal salt of L-ascorbic acid having a protecting substituent at the 5- and 6-positions. The product is separated and heated with an inorganic or organic acid to remove the protecting substituent at 5- and 6-positions. A mono-alkali metal salt or alkaline earth metal salt of L-ascorbic acid-2-sulfate is thereby obtained. This product can be converted to the di-alkali metal salt or alkaline-earth metal salt of L-ascorbic acid-2-sulfate.

The following are the novel and important embodiments of the present invention.

1. Mono- or di-alkali metal salts or alkaline earth metal salts of L-ascorbic acid-2-sulfate are preferably produced by reacting L-ascorbic acid in which the 5- and 6-positions are protected by a ketone or aldehyde, with a dimethyl formamide-sulfur trioxide complex with an inert solvent, so as to produce a sulfate, and then neutralizing the product with an alkali metal hydroxide or an alkaline earth metal hydroxide, and then removing the protecting substituent at 5- and 6-positions.

2. The compound is also preferably produced by reacting L-ascorbic acid in which the 5- and 6-positions are protected by a ketone or aldehyde with dimethyl formamide-sulfur trioxide complex which is produced by reacting of chlorosulfonic acid, dimethyl formamide and tertiary amine, so as to produce a sulfate and then neutralizing the sulfate with an alkali metal hydroxide or an alkaline earth metal hydroxide followed by removal of the protecting substituent at 5- and 6-positions.

The resulting products can be shown by the formula

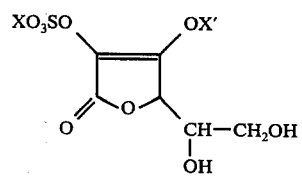

wherein X represents an alkali metal or an alkaline earth metal, and X' is hydrogen, an alkali metal or an alkaline earth metal, particularly lithium, potassium or sodium or beryllium, magnesium, calcium, barium or strontium.

When a tertiary amine such as pyridine is directly admixed with chlorosulfonic acid, tertiary amine-sulfur trioxide complex such as pyridine-sulfur trioxide complex is formed. Even though dimethyl formamide is added after forming such pyridine-sulfur trioxide complex in the reaction of the L-ascorbic acid in which the 5- and 6-positions are protected by a ketone or aldehyde with the mixture of pyridine-sulfur trioxide complex, the yield of the product is low and the product in the reaction mixture is hardly crystallized.

On the contrary, when a tertiary amine such as pyridine is mixed with dimethyl formamide and then chlorosulfonic acid is added to the mixture, dimethyl formamide-sulfur trioxide is formed as well as the case adding the tertiary amine to a mixture of dimethyl formamide and chlorosulfonic acid. When the mixture is used for the reaction of L-ascorbic acid in which the 5- and 6-positions are protected by a ketone or aldehyde the yield of the product is remarkably high and the product in the reaction mixture is crystallized in high degree.

In the present invention, the dimethyl formamide-sulfur trioxide complex is used as a sulfating agent whereby excellent result can be attained. However, when the other sulfating agents are used instead of the dimethyl formamide-sulfur trioxide complex, inferior results were found as follows.

| Sulfating agent | Result |
| --- | --- |
| Sulfuric anhydride | Large amount of decomposed material is formed and the product can not be separated by crystallization. Yield 5 to 10% |
| Chlorosulfuric acid | " Yield 5 to 10% |
| Sulfuryl chloride | " Yield 10 to 20% |

Having generally described the invention, a more complete understanding can be obtained by reference to certain specific examples, which are included for purposes of illustration only and are not intended to be limiting unless otherwise specified.

EXAMPLE 1

9.6 g of pyridine was dissolved in 300 ml of dimethyl formamide and 7.0 g of chlorosulfonic acid was added dropwise to the solution at 0° – 10° C 13.0 g of 5,6-O-isopropylidene-L-ascorbic acid was added to the reaction mixture and the mixture was stirred at room temperature for 8 hours. 2N KOH was added to the solution to adjust the pH to 7.0. The product was filtered, the filtrate concentrated, and dissolved in water, and 2N HCl was added to the resulting solution to adjust the pH to 2.3. The solution was stirred at 60° C for 45 minutes and then concentrated under reduced pressure. The residue was recrystallized from water and methanol to give 11.0 g of white needle-like crystals of mono-potassium L-ascorbic acid-2-sulfate having a decomposition point of 55° C.

EXAMPLE 2

The mono-potassium salt of 5,6-O-isopropylidene-L-ascorbic acid-2-sulfate, prepared in accordance with the process of Example 1, was dissolved in 7 ml of water and the solution stirred at 60° C for 45 minutes. 2N KOH was added to the solution to adjust the pH to 7.0, and then methanol was added, whereby 8.0 g of white flake crystals of the di-potassium salt of L-ascorbic acid-2-sulfate having a decomposition temperature of 136° – 140° C was obtained.

EXAMPLE 3

In accordance with the process of Example 1, the sulfation was carried out by using 9.6 g of pyridine, 300 ml of dimethyl formamide, 7.0 g of chlorosulfonic acid and 10.8 g of 5,6-O-isopropylidene-L-ascorbic acid. 2N NaOH was added to the resulting solution to adjust the pH to 7.0 and the product was filtered, the filtrate concentrated and dissolved in water. 2N HCl was added to the solution to adjust the pH to 2.3 and the solution was stirred at 60° C for 45 minutes and cooled. 2N NaOH was added to the solution to adjust the pH to 7.0 and methanol was added, whereby 14.6 g of white needle-like crystals of the di-sodium salt of L-ascorbic acid-2-sulfate having a melting point of 70° – 73° C was obtained.

EXAMPLE 4

The mono-potassium salt of 5,6-O-isopropylidene-L-ascorbic acid-2-sulfate, prepared in accordance with the process of Example 1 by using 5.4 g of 5,6-O-isopropylidene-L-ascorbic acid, was dissolved in 7 ml of water and the solution was stirred at 60° C for 45 minutes and cooled. A saturated solution of calcium hydroxide was added to the solution to adjust the pH to 7.0, and then methanol was added, whereby 6.91 g of white powder crystals of the mono-calcium salt of L-ascorbic acid-2-sulfate having a decomposition point of 70° – 72° C was obtained.

EXAMPLE 5

In accordance with the process of Example 1 except using 6.5 g of 5,6-O-isopropylidene-L-ascorbic acid instead of 5,6-O-isopropylidene-L-ascorbic acid, 5.4 g of mono-potassium salt of L-ascorbic acid-2-sulfate having a decomposing point of 55° C was obtained.

EXAMPLE 6

28.8 g of pyridine was dissolved in 900 ml of dimethyl formamide and then 21.0 g of chlorosulfonic acid was added dropwise to the solution at 0° to 10° C. 38.4 g of 5,6-O-cyclohexylidene-L-ascorbic acid was added to the solution. The mixture was stirred at room temperature for 8 hours and then 1N-NaOH was added to neutralize it. The precipitate was filtered and the filtrate was concentrated under a reduced pressure to form a syrup. The syrup was dissolved in 300 ml of water and then $1N-H_2SO_4$ was added to the solution to adjust pH 2.0. The solution was heated 60° C with stirring for 1 hour to remove the protective group at 5- and 6-positions and then 1N-NaOH was added to neutralize it and the solution was concentrated under a reduced pressure. The residue was dissolved in 30 ml of water and the solution was heated to 60° C and 50 ml of methanol at 60° C was added to the solution and the mixture was cooled to give 42.2 g of white needle-like crystals of di-sodium L-ascorbic acid-2-sulfate having a melting point of 130° to 140° C and a decomposition temperature of 185 to 190° C (Yield 83.8%).

| Elemental Analysis | $C_6H_6O_9SNa_2 \cdot 2H_2O$ | |
| --- | --- | --- |
| | Calculated (%) | Found (%) |
| C: | 21.44 | 21.23 |
| H: | 3.00 | 2.98 |

EXAMPLE 7

In accordance with the process of Example 6 except varying molar ratio of pyridine or triethylamine to chlorosulfonic acid, the di-sodium-ascorbic acid-2-sulfate was produced.

The results are as follows:

Table 1

| Example No. | Tertiary amine | Molar ratio (tert.amine: ClSO$_3$H) | Yield (%) |
|---|---|---|---|
| 7 – 1 | pyridine | 1 : 1 | 60 |
| 7 – 2 | pyridine | 2 : 1 | 83 |
| 7 – 3 | triethylamine | 1 : 1 | 81.5 |

EXAMPLE 8

14 g of chlorosulfonic acid was gradually added dropwise to 600 ml of dimethyl formamide at $-10°$ C to $10°$ C, and then 19.2 g of pyridine was added to the solution at room temperature and then 25.6 g of 5,6-O-cyclohexylidene-L-ascorbic acid was added to the solution at room temperature and the mixture was stirred for 8 hours, and then 1N-NaOH was added to neutralize it. The precipitate was filtered and the filtrate was concentrated under a reduced pressure to form a syrup. The syrup was dissolved in 100 ml of water and 1N-H$_2$SO$_4$ was added to the solution to adjust pH 2.0. The solution was heated to $60°$ C with stirring for 1 hour to remove the protective group at 5- and 6-positions, and then the solution was cooled and 1N-NaOH was added to neutralize it and then the solution was concentrated under a reduced pressure. The residue was dissolved in 20 ml of water and the solution was cooled to give 32 g of white needle-like crystals of di-sodium L-ascorbic acid-2-sulfate having a melting point of $70°$ to $73°$ C and a decomposition temperature of $185°$ to $193°$ C (Yield 86%)

| Elemental Analysis | C$_6$H$_6$O$_9$SNa$_2$ . 4H$_2$O | |
|---|---|---|
| | Calculated (%) | Found (%) |
| C: | 19.36 | 19.40 |
| H: | 3.79 | 3.74 |

EXAMPLE 9

In accordance with the process of Example 8, 21.6 g of 5,6-O-isopropylidene-L-ascrobic acid was used instead of 5,6-O-cyclohexylidene-L-ascorbic acid, to give 31.6 g of di-sodium L-ascorbic acid-2-sulfate.

Comparative Test 7.0 g of chlorosulfonic acid was added dropwise to 9.6 g of pyridine at $-20°$ C to $-10°$ C. After the addition, 300 ml of dimethyl formamide was added to dissolve the product. 12.8 g of 5,6-O-cyclolhexylidene-L-ascorbic acid was added to the solution and the mixture was stirred at room temperature for 8 hours and then 1N-NaOH was added to the solution to neutralize it. The precipitate was filtered and the filtrate was concentrated under a reduced pressure to form a syrup. The syrup was dissolved in 50 ml of water and 1N-H$_2$SO$_4$ was added to the solution to adjust pH 2.0. The solution was heated to $60°$ C with stirring for 1 hour to remove the protective group at 5- and 6-positions, and then 1N-NaOH was added to neutralize it and the solution was concentrated under a reduced pressure. The residue was dissolved in 10 ml of water and the solution was cooled but no crystal was given. According to the analysis of TLC using developer of n-butanol:water:acetic acid of 5 : 3 : 2, the yield was about 40 to 45%. The result shows that when pyridine was reacted with chlorosulfonic acid to form pyridine-SO$_3$, and the pyridine-SO$_3$ was used in dimethylformamide for sulfating 5,6-O-cyclohexylidene-L-ascorbic acid, the yield was quite low and the product was not crystalized.

The compounds obtained in the present process supply sulfate groups to steroid materials, such as anticoagulants, having a heparin-like effect, antihemostat, cholesterol, etc. so as to improve their metabolism in the human and animal body. They are also biologically active in animal bodies. In foul they have an effect on the eggs laid by the birds, causing a strengthening of the eggshells. This effect is superior to the use of the addition of Vitamin C to the foul feeds, because Vitamin C tends to be readily decomposed, particularly in the summer months. These compounds are also useful as additives for food, feed and cosmetic materials.

The damage to eggshells during transportation is higher than 5%. It is therefore quite important from an economical viewpoint to strengthen the shells to prevent breakage.

The novel compounds of this invention are useful for the prevention of egg breakage by strengthening the shells of the eggs laid by the birds which are administered effective amounts of the results of this invention. This effect can be obtained by adding 1–100 ppm, preferably 10–50 ppm, of the compounds of this invention in feed or in drinking water of domestic fowl, especially hens. Injection of from 0.5 to 5 mg of the compound into each hen is also effective. When the compound is added to the bird's feed or drinking water, it is preferable to prepare a master batch containing the compound along with an additive such as lactose, wheat flour, talc, starch, powdery feed, an emulsifier, etc.

The following experiment was conducted to determine the effectiveness of the compounds of this invention in preventing the breaking of egg shells.

500 of hens (White leghorn), 36 weeks of age were divided into five groups of 100 hens each. Each composition of basal ration of Table 1 was admixed with 30 ppm of vitamin-C, or 30 ppm of the mono-potassium salt, the di-sodium salt or the di-calcium salt of L-ascorbic acid-2-sulfate kept at room temperature for 30 days. The compositions were then fed to each group of hens. After 30 days and 60 days from the initiation of feeding these compositions, the strength and thickness of the individual eggshells in each group of eggs were measured. The average strength and average thickness of the eggshells in each group are shown in Table 2.

Table 1

| Composition of Basal Ration | |
|---|---|
| Ingredient | % of Diet (Complete laying mash) |
| Corn | 15.00 |
| Oats | 15.00 |
| Soybean mean | 15.00 |
| Wheat | 10.00 |
| Fish meal | 7.00 |
| Tapioca flour | 6.00 |
| Corn glutten feed | 5.50 |
| CaCO$_3$ | 4.50 |
| Wheat bran | 3.25 |
| Molasses | 3.00 |
| Wheat middlings | 2.75 |
| Dehydrated alfalfa mean | 2.75 |
| Mineral Mixture | 1.00 |
| | 100.00 |
| **Composition: Mineral | % |

Table 1-continued

| | |
|---|---|
| CaHPO$_4$ | 65.0 |
| CaCO$_3$ | 19.5 |
| Iodized salt | 13.5 |
| Trace element mixture | 2.0 |
| | 100.00 |

Table 2

| Additive | Item of test | After 30 days | After 60 days |
|---|---|---|---|
| None | strength | 3.51 kg (100%) | 3.49 kg (100%) |
| | thickness | 0.331 mm (100%) | 0.330 mm (100%) |
| 30 ppm Vitamin-C | strength | 3.54 kg (100.8%) | 3.50 kg (100.2%) |
| | thickness | 0.339 mm (102.4%) | 0.339 mm (102.7%) |
| 30 ppm mono-potassium salt of L-ascorbic acid-2-sulfate | strength | 3.86 kg (109.9%) | 3.85 kg (110.3%) |
| | thickness | 0.356 mm (107.5%) | 0.357 mm (108.0%) |
| 30 ppm di-sodium salt of L-ascorbic acid-2-sulfate | strength | 3.86 kg (109.9%) | 3.88 kg (111.2%) |
| | thickness | 0.357 mm (107.8%) | 0.358 mm (108.5%) |
| 30 ppm calcium salt of L-ascorbic acid-2-sulfate | strength | 3.88 kg (110.5%) | 3.90 kg (111.7%) |
| | thickness | 0.359 mm (108.4%) | 0.362 mm (109.7%) |

When the strength of eggshells exhibit increases of 10% over those of the standard (non-additive), the breaking of eggshells in transportation is completely eliminated. In Table 2, the percentages of the strength and thickness are based on those of the standard (non additive).

The mono- and di-sodium salts and calcium salt of L-ascorbic acid-2-sulfate produced by the process of this invention, impart no potassium problem, as compared to known potassium salts of L-ascorbic acid-2-sulfate. They have high anti-hygroscopic and antioxidative properties and are quite stable in medicinal formulations, as well as in feed, foods and cosmetic compositions.

Having now fully described the invention, it will be apparent to one of ordinary skill in the art that many changes and modifications can be made thereto without departing from the spirit or scope of the invention as set forth herein.

What is claimed as new and desired to be secured by Letters Patent is:

1. A process for producing a mono- or di-alkali metal salt or alkaline earth metal salt of L-ascorbic acid-2-sulfate which comprises:
    A. reacting L-ascorbic acid in which the 5 and 6 positions are protected by a ketone or aldehyde, with dimethyl formamide-sulfur trioxide complex produced by mixing dimethyl formamide and chlorosulfonic acid in an inert solvent and thereafter adding a dehydrohalogenating agent of a tertiary amine, so as to produce a sulfate, and
    B. neutralizing the product with an alkali metal hydroxide or an alkaline earth metal hydroxide, and
    C. removing said protecting aldehyde or ketone at the 5- and 6-positions.

2. The process according to claim 1 wherein the tertiary amine is pyridine, triethylamine or dimethyl aniline.

3. The process according to claim 1 wherein the molar ratio of the L-ascorbic acid in which the 5- and 6-positions are protected by a ketone or aldehyde to the dimethyl formamide-sulfur trioxide complex in the reaction is in the range of 1 : 1 to 2.

4. The process according to claim 1 wherein the reaction temperature in the sulfating reaction is in the range of −40° C to 100° C.

5. The process according to claim 1 wherein the inert solvent is dimethyl formamide, dioxane or tetrahydrofuran.

6. A process according to claim 2 wherein the tertiary amine is pyridine.

* * * * *